United States Patent [19]

de Cooker et al.

[11] 4,266,052

[45] May 5, 1981

[54] PROCESS FOR PREPARING CYANURIC ACID

[75] Inventors: Mario G. R. T. de Cooker; Anita G. W. G. Haemers, both of Geleen, Netherlands

[73] Assignee: Stamicarbon, B.V., Geleen, Netherlands

[21] Appl. No.: 110,500

[22] Filed: Jan. 8, 1980

Related U.S. Application Data

[63] Continuation of Ser. No. 903,399, May 8, 1978, abandoned.

[30] Foreign Application Priority Data

May 9, 1977 [NL] Netherlands ............ 7705049

[51] Int. Cl.³ .................................... C07D 251/32
[52] U.S. Cl. .................................... 544/192
[58] Field of Search ............................ 544/192

[56] References Cited

U.S. PATENT DOCUMENTS

| | | | |
|---|---|---|---|
| 4,093,808 | 6/1978 | Nelson | 544/192 |
| 4,112,232 | 9/1978 | de Cooker | 544/192 |

Primary Examiner—John M. Ford
Attorney, Agent, or Firm—Cushman, Darby & Cushman

[57] ABSTRACT

An improved process for the preparation of cyanuric acid in which urea/biuret is converted into cyanuric acid but wherein the co-production of the impurities, ammelide and ammeline is significantly reduced. Cyanuric acid is prepared by heating urea/biuret in a suitable polar organic solvent in the presence of an ammonium-, alkali metal- or alkaline-earth metal nitrate.

6 Claims, 1 Drawing Figure

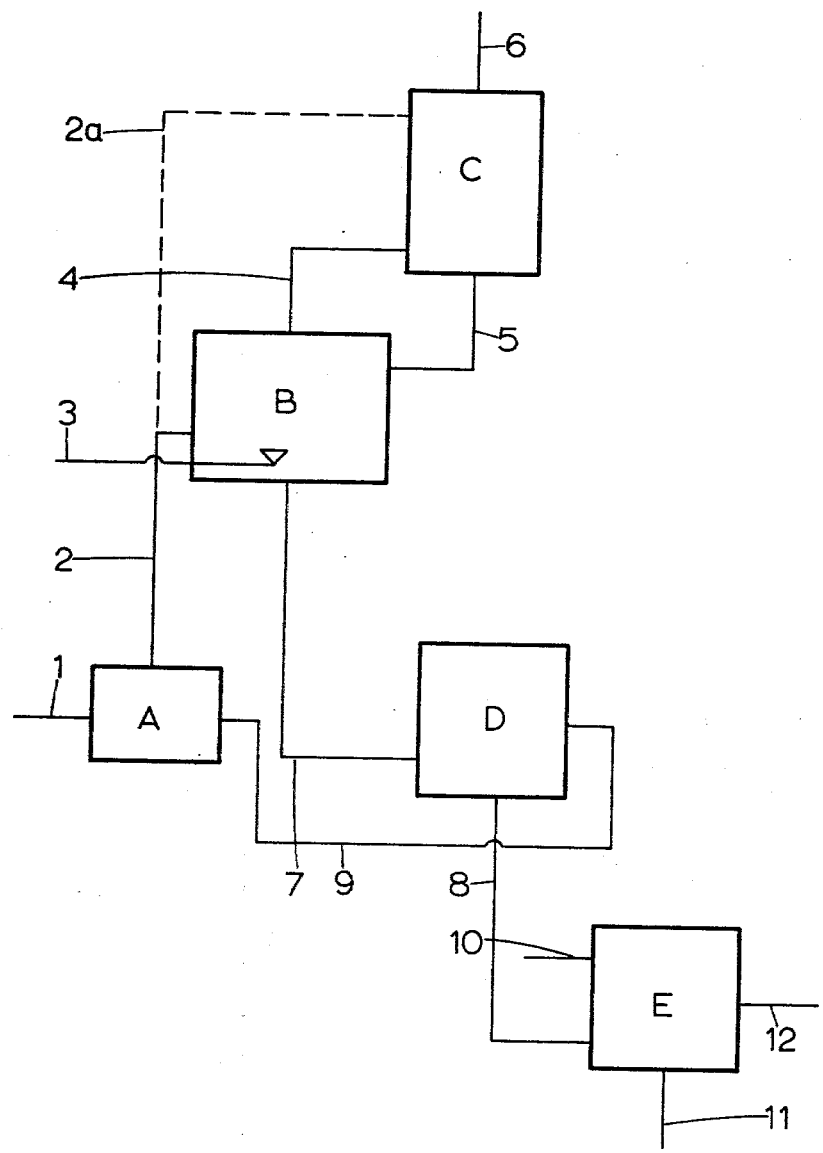

PROCESS FOR PREPARING CYANURIC ACID

This is a continuation of application Ser. No. 903,399, filed May 8, 1978, now abandoned.

The present invention relates to a process for preparing cyanuric acid by heating urea and/or biuret in a polar organic solvent. An example of a process of this general type is disclosed in Netherlands Patent Application No. 7,405,629.

BACKGROUND OF THE INVENTION

Commercial applications of cyanuric acid require that the acid contain as low as possible amounts of the impurities, ammelide and ammeline. Cyanuric acid produced according to the process disclosed in the above-mentioned Netherlands Patent Application may contain commercially unacceptable amounts of the impurities, ammelide and ammeline. It is possible to remove these impurities from cyanuric acid by treatment with a strongly acid aqueous solution to hydrolyze the ammelide and ammeline into cyanuric acid. However, such a hydrolysis step is expensive.

It is therefore an objective of the present invention to prepare cyanuric acid by heating a solution of urea and/or biuret in a polar organic solvent while reducing the amounts of the co-produced ammelide and ammeline.

DESCRIPTION OF THE INVENTION

It has been discovered that cyanuric acid with a considerably reduced ammelide and ammeline content can be obtained by conducting the reaction in the presence of an ammonium-, alkali metal- and/or alkaline-earth metal nitrate dissolved in the reaction medium.

The process according to the present invention offers the advantage that it is less dependent of the process parameters thus allowing for the use of optimum process conditions without having to carry out the expensive after-hydrolysis of the co-produced ammelide and ammeline. By following the process of the present invention, the economics especially in a continuous commercial process can be substantially improved as the reaction conditions may also be changed by employing, for example, higher urea concentration, higher temperatures, and a higher reaction rate. While the ammelide content in the cyanuric acid product may increase thereby, it will still remain within acceptable limits without necessitating an after-hydrolysis treatment.

The process according to the present invention uses a solvent in which the urea and/or biuret are relatively much more soluble than cyanuric acid. The solvent must be thermally stable under the reaction conditions and should preferably be chemically inert. The solvent must have a sufficiently high boiling point so that a liquid phase is maintained during the reaction. Suitable solvents are, e.g., dialkyl sulphones or cyclic sulphones with at most 12 carbon atoms, halogen-substituted cresols and phenols, pyrrolidones and urethanes N-substituted with phenyl or alkyl groups with at most 6 carbon atoms, cyclic urethanes, polyether alcohols and cyclic polyethers and cyclohexanol or substituted cyclohexanols with one or more hydrocarbon groups with at most 6 carbon atoms as substituents. The hydrocarbon groups are preferably phenyl, alkyl or cycloalkyl groups. Examples of suitable solvents are dimethyl sulphone, dipropyl sulphone, sulpholane, chlorocresols, 5-methyl-2-oxazolidinone, diethylene-glycol monomethyl ether, diethylene-glycol diethyl ether, 2-methyl cyclohexanol, 2,6-dimethyl cyclohexanol and 2,4,6-trimethyl cyclohexanol. Sulpholane or a derivative of it substituted with one or more methyl groups are particularly suitable.

The nitrate used in the present invention may be, e.g., unsubstituted ammonium nitrate, the nitrate of N-alkyl-substituted ammonium with preferably 1-6 carbon atoms per alkyl group, sodium nitrate, potassium nitrate, magnesium nitrate or calcium nitrate. Salts of, e.g., lithium, strontium and barium may also be used. Special preference is given to unsubstituted ammonium nitrate. The nitrate concentration should be in the range of about 0.1% by weight to about 50% by weight of the solvent, and should be preferably in the range of about 0.5% by weight to about 10% by weight of the solvent.

The concentration of starting urea and/or biuret should be limited as otherwise the ammelide content of the cyanuric acid will be at an unacceptable level. Concentrations of up to 750 grams per kg of solution are preferred, but higher urea and/or biuret concentrations may also be used.

At very low concentrations while an excellent product is obtained, the costs per unit of product are high. Preferably, the starting concentration of urea and/or biuret should range between about 150 and about 500 grams per kg of solution.

A catalyst, for example an acid, acid anhydride of ammonium salt, may be incorporated in the reaction mixture. Preferably, the catalyst is an acid or an acid anhydride or ammonium salt derived from an acid that is soluble in the reaction medium.

In practicing the process of the present invention, it is advantageous to lower the ammonia concentration in the reactor. This may be done in any known way, e.g., by stripping with a stripping gas such as air, nitrogen, or carbon dioxide. The stripping or boiling agents which are fed to the reactor in the liquid form, e.g., aliphatic, aromatic and mixed aliphatic-aromatic hydrocarbons with preferably 3–12 carbon atoms per molecule, such as cyclohexane, toluene, or the xylenes may also be used for stripping. The partial ammonia pressure may also be lowered by suction, viz., by using subatmospheric pressure.

The reaction temperature usually ranges between about 150 and about 280° C., preferably between about 170° and about 220° C., with even better results obtained between 175° and about 200° C. With higher temperatures, the reaction proceeds quicker, but the chance of forming undesirable by-products, such as ammelide and ammeline, and of decomposing the solvent become greater.

The reaction pressure may range, for example, between about 0.1 and about 10 atm. The reaction proceeds very well at about atmospheric pressure, e.g., a pressure of between about 0.5 and about 2 atmospheres. If it is intended to reduce the partial ammonia pressure by suction, a reaction pressure of between about 0.01 and about 0.25 atm. is preferred.

The process according to the present invention may be carried out batchwise, but can also be advantageously practiced as a continuous process.

DESCRIPTION OF THE DRAWING

A possible embodiment of a continuous process according to the present invention is shown diagrammatically in the drawing.

Urea and/or biuret are fed through conduit 1 to dissolver A, where the feed is dissolved in a nitrate solution such as ammonium nitrate solution in a polar organic solvent, such as sulpholane. The solution flows through conduit 2 to reaction vessel B which is a gas washer and converted into cyanuric acid. If desired, a stripping gas, e.g., nitrogen, and/or a condensable stripping additive, e.g., xylene, may be added to B through conduit 3. A gaseous mixture containing ammonia and solvent vapor escapes through conduit 4 and is fed to condenser C. Condensed solvent and, possibly, condensed stripping additive flow back to B through conduit 5. Condenser C is preferably a scrubber in which the washing liquid used may be the solution of urea and/or biuret in the polar organic solvent which is supplied through conduit 2a. Non-condensed gas escapes from C through conduit 6. This gas consists virtually of pure ammonia or an ammonia/stripping gas mixture from which ammonia can readily be recovered.

A suspension of cyanuric acid in solvent containing ammonium nitrate flows from reactor B through conduit 7 to separator D. Here the cyanuric acid is separated off, for example, by filtration, precipitation and decantation, centrifugation, or in any suitable way. The solid product flows through conduit 8 to washing device E where the product is washed with washing liquid supplied through conduit 10. The washing liquid may be, for example, water which is discharged from the washing device through conduit 11. Pure cyanuric acid is discharged through conduit 12. The cyanuric acid product may be subjected to acid hydrolysis, e.g., with nitric acid, in order to hydrolyze the by-products ammelide and ammeline to cyanuric acid. But this is usually not necessary, since the ammeline/ammelide content of the cyanuric acid is already sufficiently low for most commercial applications. The mother liquor that is separated off in D and which may still contain unconverted urea and/or biuret and which is saturated with cyanuric acid is fed back to dissolver A through conduit 9.

Sulpholane and ammonium nitrate may be placed in B at the start of the continuous process. Solvent and nitrate are recycled with losses, if any, made up, for example, through conduits (not shown) somewhere in the recycling system, preferably in A.

The present invention will be further elucidated with reference to the following Examples and the Comparative Experiment.

EXAMPLES AND COMPARATIVE EXPERIMENT

In each of the three Examples presented in the Table below and in the Comparative Experiment, 500 g of sulpholane containing the stated percentage by weight based on the sulpholane of ammonium nitrate were heated to about 250° C. with stirring. 170 ml (N.T.P) of nitrogen were passed through the reaction mixture per hour. Then 137.5 g of urea were added with the temperature maintained at about 188° C. The pressure was equal to atmospheric pressure. After one hour the reaction was stopped by cooling in ice water. The resulting cyanuric acid product was separated off. The ammelide content of the cyanuric acid product was as is stated in the Table. The ammeline content was lower than the detection limit of the method of analysis used and therefore is not presented in the Table.

| Example | Ammonium Nitrate Concentration % by weight | Urea Conversion % | Ammelide Content of Cyanuric Acid Product % by weight |
|---|---|---|---|
| I | 30 | 16 | 0.4 |
| II | 10 | 30 | 0.2 |
| III | 1 | 33 | 0.3 |
| Comparative Experiment | — | 62 | 2.2 |

It is apparent from the Comparative Experiment which was conducted with no ammonium nitrate present in the reaction vessel, that the presence of the ammonium nitrate does substantially reduce the co-production of the impurities ammelide and ammeline.

Various modifications of the process of the invention may be made without departing from the spirit or scope thereof and it should be understood that the invention is intended to be limited only as defined in the appended claims.

What is claimed is:

1. In a process for preparing cyanuric acid by heating at least one of urea and biuret in a suitable polar organic solvent, the improvement which comprises conducting the reaction at a temperature between about 170° C. and about 220° C. in the presence of a nitrate selected from an ammonium-, alkali metal-, alkaline- earth metal nitrate and mixtures thereof dissolved in the reaction medium, and wherein the amount of recycled cyanuric acid present in the reaction mixture does not exceed the amount soluble in said solvent at the reaction temperature.

2. The process of claim 1, wherein the solvent is selected from dialkyl sulphones or cyclic sulphones with at most 12 carbon atoms, halogen-substituted cresols and phenols, pyrrolidones or urethanes N-substituted with phenyl or alkyl groups with at most 6 carbon atoms, cyclic urethanes, polyether alcohols and cyclic polyethers and cyclohexanol or substituted cyclohexanols with one or more hydrocarbon groups with at most 6 carbon atoms as substituents.

3. The process of claim 2, wherein the solvent is sulpholane.

4. The process of claim 3, wherein the nitrate is unsubstituted ammonium nitrate.

5. The process of claim 4, wherein the nitrate concentration is between about 0.1 and about 50% by weight of the solvent.

6. The process of claim 5, wherein the nitrate concentration is between about 0.5 and about 10% by weight of the solvent.

* * * * *